United States Patent [19]

Hegde et al.

[11] Patent Number: 5,037,469

[45] Date of Patent: * Aug. 6, 1991

[54] SUBSTITUTED 3- OR 5-DIALKYLAMINO PYRIDINE COMPOUNDS

[75] Inventors: Shridhar G. Hegde, Maryland Heights; Len F. Lee, St. Charles, both of Mo.

[73] Assignee: Monsanto Company, St. Louis, Mo.

[*] Notice: The portion of the term of this patent subsequent to Dec. 5, 2006 has been disclaimed.

[21] Appl. No.: 457,598

[22] Filed: Dec. 27, 1989

[51] Int. Cl.$^5$ .................... C07D 213/55; A01N 43/40
[52] U.S. Cl. .......................................... 71/94; 546/310

[58] Field of Search ............................. 71/94; 546/310

[56] References Cited

U.S. PATENT DOCUMENTS 4,885,026 12/1989 Lee et al. ............................... 546/22

Primary Examiner—Jane T. Fan
Attorney, Agent, or Firm—James C. Bolding; Stanely M. Tarter

[57] ABSTRACT

Disclosed herein are 2- or 6-fluoromethyl-3-pyridinecarboxylate derivatives with 3- or 5-dialkylamino substitution which are useful as herbicides.

21 Claims, No Drawings

SUBSTITUTED 3- OR 5-DIALKYLAMINO PYRIDINE COMPOUNDS

This invention relates to a new class of 2,6-substituted pyridinedicarboxylic acid derivatives having activity as herbicides, to their use as herbicides, and to herbicidal compositions containing them. Pyridine derivatives have, for many years, been investigated for use in the biological sciences. Pyridine dicarboxylate compounds useful as herbicides are described in U.S. Pat. No. 4,692,184. These compounds have fluorinated methyl groups at the 2- and 6-positions and carboxylic acids or their derivatives at the 3- and 5-positions and are characterized further by a 4-position substituent in which the atom attached to the pyridine ring is a carbon atom, such as alkyl, alkoxyalkyl, alkylthioalkyl, aralkyl, and like moieties.

Other pyridine compounds include those which contain fluorinated methyl groups at the 2- and 6-positions, carboxylic acids or their derivatives at the 3- and/or 5-positions and at the 4-position have a substituent group beginning with a hetero atom selected from O, S, N and P. These compounds are likewise useful as herbicides.

Other herbicidal pyridines are those of U.S. Pat. No. 4,609,399 which have a fluorinated methyl group at the 2-position, a carboxylic acid group or derivative thereof at the 3- and/or 5-position, and alkoxy groups at the 4- and 6-positions.

More relevant to the compounds of this invention are those disclosed in U.S. Pat. No. 4,885,026; which are 5-amino pyridine 3-carboxylate derivatives in which the 5-amino group is a secondary amine; i.e., one hydrogen remains on the nitrogen.

BRIEF DESCRIPTION OF THE INVENTION

It is an object of this invention to provide novel pyridine compounds, as well as herbicidal methods and compositions utilizing such compounds, which have surprisingly superior herbicidal activity compared to the corresponding 5-monoalkylamino pyridine compounds of the prior art.

The novel compounds of this invention are useful as herbicides or intermediates which can be converted to herbicides and are represented by the generic formula

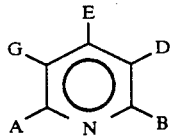

wherein:
one of A and B is selected from the group consisting of fluorinated methyl and chlorofluorinated methyl radicals, and the other is selected from the group consisting of fluorinated methyl, chlorofluorinated methyl and lower alkyl radicals;
E is selected from the group consisting of alkyl, alkenyl, cycloalkyl, cycloalkylalkyl, haloalkyl, and alkylthioalkyl radicals;
G is selected from the group consisting of carboxylic acid moieties and their alkyl ester, alkyl thioester, and alkenyl ester derivatives; and
D is —NRR' in which R and R' are the same or different lower alkyl groups, each optionally substituted with one or more groups selected from halo, amino, alkylthio, alkylsulfonyl, and alkoxy radicals.

As used herein throughout the specification and claims, the following terms have the following meanings:

The term "alkyl" means herein both straight and branched chain saturated hydrocarbon radicals having 1 to 7 carbon atoms, unless a different carbon number range is expressly stated. Examples of such radicals include, but are not limited to, ethyl, methyl, n-propyl, 1-ethylpropyl, 1-methylpropyl, n-butyl, 1,1-dimethylethyl, 2,2-dimethylpropyl, pentyl, isobutyl, isopropyl, and the like.

The term "cycloalkyl" means saturated cyclic radicals having 3 to 7 carbon atoms, such as cyclopropyl, cyclobutyl, cyclopentyl, cyclohexyl, and cycloheptyl.

The terms "alkenyl" and "alkynyl" herein mean alkenyl and alkynyl groups having 2 to 7 carbon atoms. Examples of such alkenyl groups include ethenyl, 1-propenyl, 2-propenyl, 1-butenyl, 2-butenyl, 3-butenyl, 2-methyl-1-propenyl, 2-methyl-2-propenyl, 1-methylethenyl, and the like. Examples of such lower alkynyl groups include ethynyl, 1-propynyl, 2-propynyl, and so forth.

The term "cycloalkylalkyl" is intended to mean alkyl radicals having 1 to 3 carbon atoms which is substituted with a cycloalkyl group having 3 to 7 carbon atoms.

The term "haloalkyl" is intended to mean an alkyl radical (as defined above) substituted with one or more halogen atoms selected from F, Cl, Br, and I, "haloalkenyl" and "haloalkynyl" refer to alkenyl and alkynyl radicals substituted with one or more halogens.

The term "alkanoyl" as used herein means a radical derived from an alkanoic acid, and includes formyl, acetyl (or methylcarbonyl), propanoyl (or ethylcarbonyl), cyclopropylformyl (or cyclopropylcarbonyl), and the like.

The term "cation" means any monovalent cation derived from a base which is capable of forming a salt. Typical cations include, but are not limited to, alkali metals such as sodium, potassium, and lithium; alkaline earth metals such as calcium and magnesium; and ammonium salts, organic amines, sulfonium and phosphonium salts, and other salt complexes.

The term "fluorinated methyl" means herein methyl radicals having one or more fluorine atoms attached thereto, and includes radicals wherein all hydrogen atoms replaced by fluorine.

The term "chlorofluorinated methyl" means herein a methyl radical having at least one hydrogen replaced by fluorine and at least one other hydrogen replaced by chlorine.

The term "halogen" and its combining form "halo" are used herein to refer to fluorine, chlorine, bromine, and iodine.

DETAILED DESCRIPTION OF THE INVENTION

As used throughout the specification, including the Examples, the following abbreviations have the following meanings:
LDA—lithium diisopropylamide
THF—tetrahydrofuran
DME—dimethoxyethane
DBU—1,8-diazabicyclo-[5.4.0]-undec-7-ene
DMF—N,N-dimethylformamide
ETFAA—ethyl trifluoroacetoacetate
MCPBA—m-chloroperbenzoic acid HPLC—high pressure liquid chromatography
TLC—thin layer chromatography
n-BuLi—n-butyl lithium
DMSO—dimethyl sulfoxide
Pd/C—hydrogenation catalyst which is palladium deposited on finely-divided carbon
TsCl—tosyl chloride.

Dialkylamino pyridine compounds of this invention are prepared by reduction of an alkanoyl alkylamino pyridine compound, which is in turn prepared either by reaction of a monoalkylamino pyridine with an acid chloride or by reaction of an alkanoylamino pyridine with a substituted or unsubstituted alkyl halide. The monoalkylamino pyridine, if used in the preparation, is made by reduction of an alkanoylamino pyridine, which is prepared by reaction of a 3- or 5-amino pyridine and an acid chloride. The 3- or 5-amino pyridine is prepared from a 3- or 5-chlorocarbonyl pyridine.

Aminopyridines and their preparation from the chlorocarbonyl pyridines (or pyridine acid chlorides) are described in more detail in U.S. Pat. No. 4,885,026 which corresponds to European Patent Publication No. 0252055, the disclosure of which is incorporated herein by reference.

Preparation of the chlorocarbonyl pyridines (pyridine acid chlorides) is illustrated below in Steps 1-9. Preparation of primary amino pyridines is shown below in Examples F-1 to F-3. Preparation of the alkanoyl amine precursors is shown in Examples G-1 to G-5, while Examples H-1 and H-2 illustrate preparation of monoalkylamine precursors of the compounds of this invention. Preparation of the pyridine 5-dialkylamine compounds of this invention is shown following these examples in Examples 1 to 12.

PREPARATION OF PYRIDINE 5-ACID CHLORIDE STARTING MATERIALS

The compounds of this invention are prepared using as a starting material a pyridine 3,5-dicarboxylic acid mono-ester mono-chloride or dichloride. Steps 1-9 which follow set out in detail the preparation of three specific acid halides which are used as starting materials for the compounds of this invention. Other acid halides may be readily prepared using the procedures of Steps 1-9 by varying the ketoester and aldehyde used in Step 1 to obtain the desired substituents in the pyridinedicarboxylate product. Other suitable pyridinecarboxylate acid halide starting materials are shown in U.S. Pat. No. 4,692,184 in Examples 44-51 and 82-83 inclusive, the disclosure of which is incorporated herein by reference in its entirety. Other acid halide starting materials may be readily prepared using the techniques set out in that U.S. Patent.

The following Steps 1-9 illustrate an example of the procedures for preparation of the acid halide compounds which are the starting materials for making the amines of the present invention. In these steps, a β-ketoester is reacted with an aldehyde to form a pyran (Step 1). The pyran is then reacted with ammonia to form a dihydroxypiperidine (Step 2), which is dehydrated to make a dihydropyridine compound (Step 3). The dihydropyridine is then oxidized or dehydrofluorinated to prepare a pyridinedicarboxylate compound (Step 4).

The ester groups of the pyridinedicarboxylate compound are the ester groups of the β-ketoester, and the 4-position of the pyridine is substituted with the same substituent as is on the aldehyde reagent.

When the pyridinedicarboxylate is substituted at the 2- or 6-position with a trifluoromethyl radical and at the other of these positions with a difluoromethyl radical, hydrolysis of the pyridine dicarboxylate compound occurs selectively on the side having the $CF_2H$ group when one equivalent of a base such as KOH is employed in the hydrolysis (Step 8). When two equivalents of base or more are employed, the dicarboxylate is hydrolyzed to the diacid (Step 5). The diacid may be converted to the diacid chloride by treatment with a chlorinating agent such as $SOCl_2$ or $PCl_5$. Following this conversion, treatment with one equivalent of an alcohol selectively esterifies the diacid chloride on the chloride group adjacent to the $CF_2H$ group.

STEP 1

Preparation of dimethyl 2,6-bis(trifluoromethyl)-2,6-dihydroxy-4-isobutyl-tetrahydro-3,5-pyrandicarboxylate To a mechanically stirred mixture of 280 g (2.0 mole) of 80% pure methyl trifluoroacetoacetate and 86 g (1.0 mole) of isovaleraldehyde is added 1 ml of piperidine. An exothermic reaction occurs and the temperature of the reaction mixture reaches 105° C. After 5 hours of stirring, the reaction mixture is triturated with 450 ml of hexane and 30 ml of ether and cooled with a dry ice bath to give 1.68 g of a first crop, m.p. 83°–87° C. and 14.51 g of a second crop, m.p. 67°–73° C.

The first crop is the desired product which contains a mixture of 5:1 cis and trans isomers.

The second crop is a 2:1 mixture of cis and trans isomers. The mother liquor is concentrated to give 344 g of a residue which is a crude mixture of cis and trans isomer of the desired product.

STEP 2

Preparation of dimethyl 2,6-bis(trifluoromethyl)-2,6-dihydroxy-4-isobutyl-3,5-piperidinedicarboxylate To a solution of 344 g (0.920 mole) crude product from Step 1 in 500 ml of tetrahydrofuran (THF) is passed 58 g (3.41 mole) of gaseous ammonia for 3 hours. The reaction mixture is concentrated and the residue (332 g) is recrystallized from hexane-ether to give 53.7 g (13% yield from methyl trifluoroacetoacetate) of the desired product as a white solid, m.p. 102°–106° C.

The mother liquor is concentrated to provide more of the crude desired product.

STEP 3

Preparation of a 2:1 mixture of dimethyl 2,6-bis(trifluoromethyl)-1,4-dihydro-4-isobutyl-3,5-pyridinedicarboxylate and its 3,4-dihydropyridine isomer To an ice water cooled mixture of 200 ml of concentrated sulfuric acid and 200 ml of methylene chloride is added 48.7 g (0.115 mole) of the product of Step 2 at once. The reaction mixture is stirred for 20 minutes and poured into 1 L of ice water. The methylene chloride layer is separated and washed once with 100 ml of saturated sodium bicarbonate, dried and concentrated to give 28.0 g (64.6%) of crude product. A portion (5.0 g) of this product is kugelrohr distilled at 0.5 torr (pot temperature at 120° C.) to give 4.8 g of the desired product, $n_D^{25}$ 1.4391.

Step 3 product may be prepared in better overall yield without isolation of Step 1 and Step 2 product by the following procedure:

To a mechanically stirred mixture of 340.3 g (1.98 mol) of 98.9% pure methyl trifluoroacetoacetate (MTFAA), 100 mL of toluene and 0.86 g (0.01 mol) of piperidine was added 90.5 g (1.03 mol) of isovaleraldehyde in 20 minutes. The reaction mixture exothermed causing a rise of temperature to 83° C. The reaction mixture was maintained at 80° C. for 3 hours. $^{19}$F NMR showed that the reaction was 89% complete. Heat was removed, and the reaction mixture was diluted with 125 mL of toluene and stirred overnight (16 hours). Gaseous ammonia was passed through the reaction mixture, the exotherm caused a rise of temperature to 68° C. in 50 minutes. A water cooling bath was applied to the reaction vessel to reduce the reaction temperature to 53° C. while ammonia was passed continuously. A total of 47.3 g (2.78 mol) of ammonia was passed in 1.5 hours. The reaction mixture was diluted with 100 mL of toluene. A Claisen distillation head was attached to the reaction vessel.

Excess ammonia and parts of toluene were removed in vacuo (water aspirator) while temperature was maintained at 26° C. An additional 200 mL of toluene was added, and the distillation was continued to remove a total of 200 mL of distillate in 1.5 hours. The reaction mixture was diluted with 100 mL of toluene and cooled to 5° C. with an ice bath. Sulfuric acid (453 g, 4.53 mol) was added in 5 minutes. The exotherm caused the temperature to rise to 25° C. The temperature gradually subsided to 5° C. in 10 minutes and was maintained at 5° C. for 40 minutes. An additional 95 g (0.95 mol) of sulfuric acid was added, and the reaction mixture was stirred at 5° C. for 20 minutes before being poured into a mixture of 500 mL of toluene and 2 L of ice water. The toluene layer was separated and the aqueous layer was extracted once with 500 mL of toluene. The combined toluene extracts were washed successively with 500 mL of water, 500 mL of saturated aqueous NaHCO$_3$, 500 mL of brine and concentrated in vacuo to afford 363.6 g of an oil. GC area percent analysis indicated that the oil contained 9% of 3,4-dihydropyridine isomer and 75.4% of 1,4-dihydropyridine isomer corresponding to an overall yield of 82.9% from MTFAA.

STEP 4

Preparation of dimethyl 2-(difluoromethyl)-6-(trifluoromethyl)-4-isobutyl-3,5-pyridinedicarboxylate

(a) Reaction of the Product of Step 3 with DBU

A mixture of 23.0 g (0.0591 mole) of the product of Step 3, 12.2 g (0.077 mole) of 96% pure DBU, and 100 ml of THF is held at reflux for 3 days and poured into 250 ml of 3N HCl. The oil precipitate is extracted into ether (2×100 ml). The ether extracts are dried (MgSO$_4$) and concentrated to give 14.4 g of an oil which, according to $^1$H NMR, contained the desired product and acidic products. This oil is dissolved in ether and extracted with 100 ml of saturated sodium bicarbonate. The ether layer is dried (MgSO$_4$) and concentrated to give 8.9 g of an oil which is 71% pure desired product (by $^{19}$F NMR).

The sodium bicarbonate extract is acidified with concentrated HCl to give an oil which is extracted into ether. The ether layer is dried (MgSO$_4$) and concentrated to give 4.8 g of a residue which contained monocarboxylic acid and dicarboxylic acid (9:1) derived from the desired product. This residue is treated with 3.0 g (0.0217 mole) of potassium carbonate, 20 ml of methyl iodide, and 50 ml of acetone. The mixture is held at reflux for 42 hours and concentrated. The residue is treated with water and extracted with ether (2×100 ml). The ether layer is dried and concentrated. The residue is kugelrohr distilled at 1 torr (pot temperature of 130° C.) to give 5.1 g (23.4% from Step 3) of the desired product as an oil, n$_D^{25}$ 1.4478. This product crystallizes after standing, m.p. 36°–37° C.

The 71% pure desired product described previously was purified by HPLC using 3% ethyl acetate/cyclohexane as eluent to give an earlier fraction (0.79 g, retention time 7–8.5 minutes) which was identified as methyl 6-(difluoromethyl)-4-(isobutyl)-2-(trifluoromethyl)-3-pyridinecarboxylate. The second fraction (retention time 8.5–18.5 minutes) is an additional 6.4 g (29.4%) of pure desired product, n$_D^{25}$ 1.4474.

(b) Reaction of the Product of Step 3 with Tributylamine

A mixture of 38.9 g of an 80% pure product of Step 3 and 20.5 g of tributylamine is heated to 155° C. in 30 minutes. The reaction mixture was cooled to 30° C. and diluted with 100 ml of toluene. The toluene solution is washed successively with 6N hydrochloric acid, saturated sodium bicarbonate, and brine, dried and concentrated to give 36.4 g of a 73% pure product which corresponds to an 86% yield. This reaction can also be carried out in excess of tributylamine (10 equivalents) giving essentially similar results.

(c) Reaction of the Product of Step 3 with Tributylamine in Toluene

A mixture of 38.9 g of an 80% pure product of Step 3, 20.4 g of tributylamine and 30 ml of toluene is heated to 115° C. in 40 minutes and held at 115° C. for 1 hour and 40 minutes. The reaction mixture is cooled and worked up as in (b) above to give 36.3 g of a 76% pure product which corresponds to a 90% yield.

(d) Reaction of the Product of Step 3 with Tributylamine

A mixture of 11.8 g of an 80% pure product of Step 3 and 3.34 g of triethylamine is heated at 100° C. for 10 minutes, then at 125° C. for 10 minutes. The reaction mixture was cooled and worked up as in (b) above to give 8.14 g of a 76% pure product which corresponds to a 63% yield.

(e) Reaction of the Product of Step 3 with 2,6-Lutidine in the Presence of a Catalytic Amount of DBU A mixture of 5.0 g of product of Step 3 and 2.13 g of 2,6-lutidine is heated at 143° C. for 30 minutes. Two drops of DBU are added and the reaction mixture is heated for additional 1 hour and 30 minutes, cooled and worked up as in (b) above to give 4.23 g of the desired product. The reaction can also be carried out in excess of 2,6-lutidine and catalytic amount of DBU without solvent or in the presence of toluene as solvent giving similar results.

STEP 5

Preparation of
2-(difluoromethyl)-6-(trifluoromethyl)-4-isobutyl-3,5-pyridinedicarboxylic acid A 5-liter flask was charged with 894 g (2.42 mol) of the compound of Step 4 and 1 liter of water. To this was added a solution of 574 g (8.7 mol) of KOH in 800 ml of water. The mixture was refluxed overnight, after which HPLC showed that the reaction was complete. The flask was cooled to room temperature, acidified with HCl, and stirred until the organic phase solidified. The solids were filtered, washed with water, and dried in a fluid bed dryer. The diacid was obtained (756 g, 91.6% yield) as a brown solid.

STEP 6

Preparation of
3,5-bis-(chlorocarbonyl)-2-(difluoromethyl)-4-isobutyl-6-(trifluoromethyl)pyridine The diacid product of Step 5 (37.06 g, 0.108 mole) was refluxed with 150 ml $SOCl_2$ for three hours. At this time, $^{19}F$ NMR indicated the reaction was complete. The excess $SOCl_2$ was removed by rotary evaporation, leaving a dark oil which was the bis-acid chloride. This was Kugelrohr distilled at 100° C. to give a colorless oil.

STEP 7

Preparation of methyl
5-(chlorocarbonyl)-2-(difluoromethyl)-4-isobutyl-6-(trifluoromethyl)pyridine-3-carboxylate The product of Step 6 was then dissolved in 100 ml THF followed by 100 ml methanol. After 2½ hours the solvent was evaporated, leaving 31.2 g white solid, m.p. 71°–75° C. in 77% yield.

STEP 8

Preparation of
2-(difluoromethyl)-4-isobutyl-6-(trifluoromethyl)-3,5-pyridinedicarboxylic acid, 5-methyl ester A 1-liter 4-necked flask was charged with 300 g of product of Step 4 and about 200 ml ethanol. In a separate flask was combined 59.14 g (0.896 mol) of 85% KOH and about 100 ml of water. The aqueous solution was poured into the organics and the flask was equipped with a mechanical stirrer, thermometer, nitrogen inlet and a water cooled conserver. The reaction mixture was heated to reflux, refluxed for 45 minutes and was cooled. The reaction mixture was concentrated and the concentrate was diluted with water and extracted once with ethyl ether. The ether extract (to remove starting material) was discarded. The aqueous solution was acidified with concentrated HCl and the orange precipitate that resulted was extracted with ethyl ether. The aqueous solution was extracted with ether 3 times. The ether extracts were combined and dried over anhydrous magnesium sulfate, filtered and concentrated to yield 253.13 g (87.5% yield) of the monoacid.

STEP 9

Preparation of methyl
2-(difluoromethyl)-3-(chlorocarbonyl)-4-isobutyl-6-(trifluoromethyl)-5-pyridinecarboxylate The acid (253 g, 0.7121 mol) from Step 8 was refluxed for 24 hours in approximately 250–300 ml of thionyl chloride. The reaction mixture was concentrated to yield 244.59 g of acid chloride in 91.9% yield. $n_D^{25}$ 1.4614.

Steps 1–9 above have illustrated the preparation of pyridine carboxylic acid chlorides having a particular set of 2,- 6,- and 4-substituents. Preparation of other acid chlorides will be clear from the foregoing and by reference to U.S. Pat. No. 4,692,184.

PREPARATION OF 5-AMINO PYRIDINES

The next step in the sequence for preparing compounds of the present invention is the conversion of the carboxylic acid chloride function of the starting materials shown above to the correspondingly-substituted 5-amino or 3,5-bis amino pyridine. The general procedure for this conversion is shown in Examples F-1 to F-3.

EXAMPLE F-1

3-Pyridinecarboxylic acid,
5-amino-2-(difluoromethyl)-4-(2-methylpropyl)-6-(trifluoromethyl)-, methyl ester To a stirred solution of 24.4 g (0.375 mol) sodium azide in 100 mL water and 200 mL of acetone at room temperature was added a solution of 55.8 g (0.15 mol) product of Step 7 above in 100 mL of acetone in portions. Following a mild exotherm, the mixture was stirred at room temperature for 4 h. The reaction mixture was concentrated, and diluted with 200 mL water. The mixture was extracted with ethyl ether (2×200 mL), and the combined extracts were washed with water (2×200 mL), dried ($MgSO_4$), and evaporated. The crude product was then vacuum distilled (130° C., 2 mm Hg) by Kugelrohr apparatus to afford 44.0 g (91%) of the desired product as a pale yellow solid; mp 48°–50° C.

The following amines were made in a similar manner using the general procedure for Example A-1 and starting with the indicated pyridine acid chloride.

EXAMPLE F-2

3-Pyridinecarbothioic acid,
5-amino-4-(2-methylpropyl)-6-(difluoromethyl)-2-(trifluoromethyl)-, S-methyl ester This compound is made from 3-pyridinecarbothioic acid, 5-(chlorocarbonyl)-4-(2-methylpropyl)-6-(difluoromethyl)-2-(trifluoromethyl)-, S-methyl ester. This compound appears as Example 168 in U.S. Pat. No. 4,885,026.

EXAMPLE F-3

3-Pyridinecarboxylic acid,
5-amino-2-(difluoromethyl)-4-(cyclopropylmethyl)-6-(trifluoromethyl)-, methyl ester 65% from 3-pyridinecarboxylic acid, 5-(chlorocarbonyl)-4-(cyclopropylmethyl)-2-(difluoromethyl)-6-(trifluoromethyl)-, methyl ester; $n_D^{25}$ = 1.5885.

PREPARATION OF ALKANOYLAMINO PRECURSORS

The alkanoyl amine precursors to compounds of this invention are made as shown in the following Examples G-1 to G-5.

EXAMPLE G-1

3-Pyridinecarboxylic acid,
2-(difluoromethyl)-5-(formylamino)-4-(2-methylpropyl)-6-(trifluoromethyl)-, methyl ester To an ice-cold solution of formic-acetic anhydride (prepared by mixing 76 mL of acetic anhydride and 38 mL of 80% formic acid) was added 9.72 g (0.03 mol) of product of Example F-1 and the mixture was stirred at room temperature for 48 h. The reaction mixture was then concentrated by distillation under vacuum (70° C., 0.7 torr) and the resulting oily residue was triturated with hexane to obtain a white solid. Recrystallization of the crude material from hexane-ether afforded 9.5 g (89%) of product as colorless crystals: mp 119°-120° C.

The compounds of Examples G-2 to G-5 below were prepared using the same general procedure as that shown in Example G-1.

EXAMPLE G-2

3-Pyridinecarboxylic acid,
5-(acetylamino)-2-(difluoromethyl)-4-(2-methylpropyl)-6-(trifluoromethyl)-, methyl ester A solution of 6.52 g (0.02 mol) of product of Example F-1 in 30 mL of acetyl chloride was stirred overnight at room temperature. Evaporation of acetyl chloride by vacuum distillation (60° C., 2 mm) and trituration of the resulting residue with hexane-ether afforded 6.78 g (92%) of product as a white solid: mp 188°-189° C.

EXAMPLE G-3

3-Pyridinecarboxylic acid,
6-(difluoromethyl)-5-(formylamino)-4-(2-methylpropyl)-2-(trifluoromethyl)-, methyl ester This compound is prepared from product of Example F-1 and formic-acetic anhydride. It appears as Example 174 of U.S. Pat. No. 4,885,026.

EXAMPLE G-4

3-Pyridinecarbothioic acid,
6-(difluoromethyl)-5-(formylamino)-4-(2-methylpropyl)-2-(trifluoromethyl)-, S-methyl ester 82% yield from product of Example F-2 as an off-white solid: mp 135°-136° (cyclohexane).

EXAMPLE G-5

3-Pyridinecarboxylic acid,
4-(cyclopropylmethyl)-2-(difluoromethyl)-5-(formylamino)-6-(trifluoromethyl)-, methyl ester 81.6% yield from product of Example F-3 as a white crystalline solid: mp 119°-120° C. (cyclohexane).

PREPARATION OF ALKYLAMINO PRECURSORS

Preparation of the monoalkyl amine compounds is shown in the following Examples H-1 and H-2.

EXAMPLE H-1

3-Pyridinecarboxylic acid,
2-(difluoromethyl)-5-(methylamino)-4-(2-methylpropyl)-6-(trifluoromethyl)-, methyl ester 61% yield from product of Example G-1 using the procedure shown under Example 1 as a pale yellow liquid: $n_D^{25} = 1.5855$.

EXAMPLE H-2

3-Pyridinecarboxylic acid,
2-(difluoromethyl)-5-(ethylamino)-4-(2-methylpropyl)-6-(trifluoromethyl)-, methyl ester Prepared similarly to the procedure shown under Example 1 in 91% yield from product of Example G-2 as a colorless liquid: $n_D^{25} = 1.5833$.

PREPARATION OF ALKYLALKANOYLAMINO PRECURSORS

EXAMPLE J-1

3-Pyridinecarboxylic acid,
5-[(cyclopropylcarbonyl)methylamino]-2-(difluoromethyl)-4-(2-methylpropyl)-6-(trifluoromethyl)-, methyl ester A solution of 6.8 g (0.02 mol) of product of Example H-1 and 2.5 g (0.024 mol) of cyclopropane carboxylic acid chlorine in 50 mL of toluene was heated at reflux for 48 h. Evaporation of the solvent under reduced pressure gave an oil which solidified upon trituration with petroleum ether. Recrystallization of the crude product from hexane afforded 5.23 g (64%) of product as a white solid: mp 74°-76° C.

EXAMPLE J-2

3-Pyridinecarboxylic acid,
2-(difluoromethyl)-5-(ethylformylamino)-4-(2-methylpropyl)-6-(trifluoromethyl)-, methyl ester To a solution of 6.37 g (0.018 mol) of product of Example G-1 in 25 mL of dry THF at −78° was added 18 mL (0.018 mol) of 1M sodium bis(trimethylsilyl)amide in THF. After 1 h, 19.5 g (0.125 mol) of ethyl iodide was added and the mixture was slowly warmed to room temperature. The solution was then heated at reflux for 10 h. after cooling to room temperature, 25 mL of saturated ammonium chloride solution was added and the mixture was extracted with ethyl acetate (3×100 mL). The combined organic layers were washed with water, dried (MgSO₄), and evaporated. Chromatographic purification of the residue afforded 5.3 g (77%) of product as a pale yellow sold: mp 61°-62° C.

EXAMPLE J-3

3-Pyridinecarboxylic acid,
5-(acetylethylamino)-2-(difluoromethyl)-4-(2-methylpropyl)-6-(trifluoromethyl)-, methyl ester A solution of 5.09 g (0.014 mol) of product of Example H-2 and 30 mL of acetyl chloride was stirred at room temperature for 60 h. The excess of acetyl chloride was evaporated, and the residue was purified by chromatography to afford 5.46 g (96%) of product as a colorless oil: $n_D^{25} = 1.5855$.

EXAMPLE J-4

3-Pyridinecarboxylic acid,
5-(cyclopropylcarbonyl)ethylamino]-2-(difluoromethyl)-4-(2-methylpropyl)-6-(trifluoromethyl)-, methyl ester A solution of 5.09 g (0.014 mol) of product of Example H-2 and 2.23 g (0.021 mol) of cyclopropane carboxylic acid chloride in 50 mL of benzene was heated at reflux for 72 h. The benzene was evaporated, and the residue was purified by chromatography to afford 5.35 g (90%) of product as a pale yellow oil: $n_D^{25} = 1.5851$.

EXAMPLE J-5

3-Pyridinecarboxylic acid, 6-(difluoromethyl)-5-(formylmethylamino)-4-(2-methylpropyl)-2-(trifluoromethyl)-, methyl ester To a solution of 7.08 g (0.02 mol) of product of Example G-3 in 20 mL of dry THF at −78° C. was added 20 mL (0.02 mol) of 1M sodium bis(trimethylsilyl)amide in THF. After 1 h, 14.2 g (0.1 mol) of methyl iodide was added and the mixture was slowly warmed to room temperature over 1 h. After stirring for 12 h at room temperature, 25 mL of saturated ammonium chloride solution was added and the mixture was extracted with ethyl acetate (3×100 mL). The combined organic layers were washed with water, dried (MgSO$_4$), and evaporated. Chromatographic purification of the residue afforded 5.6 g (76%) of product as a pale yellow solid: mp 85°–86° C.

PREPARATION OF DIALKYLAMINO PYRIDINE COMPOUNDS OF THIS INVENTION

EXAMPLE 1

3-Pyridinecarboxylic acid, 5-[(cyclopropylmethyl)methylamino]-2-(difluoromethyl)-4-(2-methylpropyl)-6-(trifluoromethyl)-, methyl ester To a solution of 3.26 g (0.008 mol) of product of Example J-1 in 20 mL of dry THF was added dropwise 10 mL (0.02 mol) of 2M borane-methyl sulfide in THF. The mixture was then heated at reflux for 8 h. The reaction was quenched by cautiously adding 5 mL of methanol while cooling in ice bath. After the frothing ceased, 10 mL of conc. HCl was added and the mixture was heated at reflux for 1 h. After cooling to room temperature, the solvent was evaporated and the residue was partitioned between 100 mL of ethyl acetate and 100 mL of 10% sodium hydroxide solution. The organic layer was washed with water, dried (MgSO$_4$), and evaporated. Purification of the residue by chromatography followed by kugelrohr distillation (1.5 torr, 115°–120° C.) afforded 1.8 g (57%) of title compound as a pale yellow oil: $n_D^{25} = 1.5925$.

The following Examples 2 to 5 were prepared according to the procedure used in Example 1.

EXAMPLE 2

3-Pyridinecarboxylic acid, 2-(difluoromethyl)-5-(ethylmethylamino)-4-(2-methylpropyl)-6-(trifluoromethyl)-, methyl ester 70% yield from product of Example J-2 as a pale yellow liquid: $n_D^{25} = 1.6175$.

EXAMPLE 3

3-Pyridinecarboxylic acid, 5-(diethylamino)-2-(difluoromethyl)-4-(2-methylpropyl)-6-(trifluoromethyl)-, methyl ester 22% yield from product of Example J-3 as a pale yellow liquid: $n_D^{25} = 1.5866$.

EXAMPLE 4

3-Pyridinecarboxylic acid, 5-[(cyclopropylmethyl)ethylamino]-2-(difluoromethyl)-4-(2-methylpropyl)-6-(trifluoromethyl)-, methyl ester 19% yield from product of Example J-4 as a colorless oil: $n_D^{25} = 1.5840$.

EXAMPLE 5

3-Pyridinecarboxylic acid, 6-(difluoromethyl)-5-(dimethylamino)-4-(2-methylpropyl)-2-(trifluoromethyl)-, methyl ester 60% yield from product of Example J-5 as a pale yellow liquid: $n_D^{25} = 1.6120$.

EXAMPLE 6

3-Pyridinecarbothioic acid, 6-(difluoromethyl)-5-(dimethylamino)-4-(2-methylpropyl)-2-(trifluoromethyl)-, S-methyl ester To a solution of 5 g (0.0135 mol) of product of Example G-4 in 25 mL of dry THF at −78° C. was added 13.5 mL (0.0135 mol) of 1M sodium bis(trimethylsilyl)amide in THF. After 1 h, 10 mL of methyl iodide was added and the mixture was slowly warmed to room temperature. After stirring overnight, 25 mL of saturated ammonium chloride solution was added and the mixture was extracted with ethyl acetate (3×100 mL). The combined organic layers were washed with water, dried (MgSO$_4$), and evaporated.

To a stirred solution of the residue from above in 10 mL of dry THF was added 15 mL (0.03 mol) of 2M borane-methyl sulfide in THF. The mixture was heated at reflux for 4 h, and then cooled in ice bath while 10 mL of methanol was added cautiously. After frothing had ceased, 10 mL of conc. HCl was added and the mixture was heated at reflux for 1 h. The reaction was cooled to room temperature, the solvent was removed by evaporation under reduced pressure, and the residue was partitioned between ethyl acetate (100 mL) and 10% sodium hydroxide solution (100 mL). The organic layer was washed with water, dried (MgSO$_4$) and evaporated. Kugelrohr distillation (0.7 torr, 120°–122° C.) of the residue afforded 3.3 g (66%) of product as a pale yellow oil: $n_D^{25} = 1.6035$.

The following compounds of Examples 7 and 8 were prepared in a manner similar to that of Example 6.

EXAMPLE 7

3-Pyridinecarboxylic acid, 2-(difluoromethyl)-5-(dimethylamino)-4-(2-methylpropyl)-6-(trifluoromethyl)-, methyl ester 61% yield from product of Example G-1 as a pale yellow liquid: $n_D^{25} = 1.6020$.

EXAMPLE 8

3-Pyridinecarboxylic acid, 4-(cyclopropylmethyl)-2-(difluoromethyl)-5-(dimethylamino)-6-(trifluoromethyl)-, methyl ester 55% yield from product of Example G-5 as a yellow liquid: $n_D^{25} = 1.5934$.

EXAMPLE 9

3-Pyridinecarboxylic acid, 4-(cyclopropylmethyl)-2-(difluoromethyl)-5-(ethylmethylamino)-6-(trifluoromethyl)-, methyl ester To a solution of 4.05 g (0.0115 mol) of product of Example G-5 in 25 mL of dry THF at −78° C. was added 11.5 mL (0.0115 mol) of 1M sodium bis(trimethylsilyl)amide in THF. After 1 h, 10 mL of ethyl iodide was added and the mixture was slowly warmed to room temperature. The solution was then heated at reflux for 10 h. After cooling to room temperature, 25 mL of saturated ammonium chloride solution was added and the mixture was extracted with ethyl acetate (3×100 mL). The combined organic layers were washed with water, dried (MgSO$_4$), and evaporated.

To a stirred solution of the residue from above in 10 mL of dry THF was added 15 mL (0.03 mol) of 2M borane-methyl sulfide in THF. The mixture was heated at reflux for 4 h, and then cooled in ice bath while 10 mL of methanol was added cautiously. After frothing had ceased, 10 mL of conc. HCl was added and the mixture was heated at reflux for 1 h. The reaction was cooled to room temperature, the solvent was removed by evaporation under reduced pressure, and the residue was partitioned between ethyl acetate (100 mL) and 10% sodium hydroxide solution (100 mL). The organic layer was washed with water, dried (MgSO$_4$), and evaporated. kugelrohr distillation (0.7 torr, 123°–125° C.) of the residue afforded 2.46 g (58%) of product as a pale yellow liquid: $n_D^{25}=1.6030$.

EXAMPLE 10

3-Pyridinecarboxylic acid, 5-[(2-aminoethyl)methylamino]-2-(difluoromethyl)-4-(2-methylpropyl]-6-(trifluoromethyl)-, methyl ester To a solution of 3.54 g (0.01 mol) of product of Example G-1 in 20 mL of dry THF at −78° C. was added 10 mL (0.01 mol) of 1M sodium bis(trimethylsilyl)amide in THF. After 1 h, a solution of 1.2 g (0.01 mol) of bromoacetonitrile in 5 mL of THF was added and the mixture was slowly warmed to room temperature. After 12 h, the reaction was quenched by the addition of 10 mL of saturated ammonium chloride solution. The mixture was diluted with water and extracted with ethyl acetate (3×100 mL). The combined organic layers were washed with water, dried (MgSO$_4$), and evaporated to obtain a yellow orange oil.

To a stirred solution of the crude product from above in 50 mL of dry THF was added 12 mL (0.024 mol) of 2M borane-methyl sulfide in THF. The mixture was heated at reflux for 5 h, and then cooled in ice bath while 10 mL of methanol was added cautiously. After frothing had ceased, 10 mL of conc. HCl was added and the mixture was heated at reflux for 1 h. The reaction was cooled to room temperature, the solvent was removed by evaporation under reduced pressure, and the residue was partitioned between ethyl acetate (100 mL) and 10% sodium hydroxide solution (100 mL). The organic layer was washed with water, dried (MgSO$_4$), and evaporated. Chromatographic purification of the residue on chromatotron afforded 0.8 g (21%) of title compound as a pale yellow oil: $n_D^{25}=1.5825$.

EXAMPLE 11

3-Pyridinecarboxylic acid, 2-(difluoromethyl)-5-[(2-hydroxyethyl)methylamino]-4-(2-methylpropyl)-6-(trifluoromethyl)-, methyl ester To a stirred solution of 7.08 g (0.02 mol) of product of Example G-1 in 50 mL of dry THF at −78° C. was added 20 mL (0.02 mol) of 1M sodium bis(trimethylsilyl)amide in THF. After 1 h at −78° C., a solution of 3.06 g (0.02 mol) of methyl bromoacetate in 5 mL of THF was added and the mixture was slowly warmed to room temperature. After 48 h, the reaction was quenched by the addition of 10 mL of saturated ammonium chloride solution. The mixture was diluted with water and extracted with ethyl acetate (3×100 mL). The combined organic layers were washed with water, dried (MgSO$_4$), and evaporated to obtain a yellow oil.

To a stirred solution of the crude product from above in 50 mL of dry THF was added 25 mL (0.05 mol) of 2M borane-methyl sulfide in THF. The mixture was heated at reflux for 8 h, and then cooled in ice bath while 20 mL of methanol was added cautiously. After frothing had ceased, 20 mL of conc. HCl was added and the mixture was heated at reflux for 1 h. The reaction was cooled to room temperature, the solvent was removed by evaporation under reduced pressure, and the residue was partitioned between ethyl acetate (100 mL) and 10% sodium hydroxide solution (100 mL). The organic layer was washed with water, dried (MgSO$_4$), and evaporated. Chromatographic purification of the residue on chromatotron afforded 3.6 g (47%) of this Example as a yellow oil: $n_D^{25}=1.5870$.

EXAMPLE 12

3-Pyridinecarboxylic acid, 2-(difluoromethyl)-4-(2-methylpropyl)-5-(methylpropylamino)-6-(trifluoromethyl), methyl ester A solution of 3.88 g (0.00114 mol) of product of Example G-1 in 25 mL of propionyl chloride was allowed to stand at room temperature overnight. Excess propionyl chloride was removed by evaporation under reduced pressure and the residue was used in the next step without further purification.

To a solution of the above residue in 15 mL of dry THF at 0° C. was added 12 mL (0.024 mol) of 2M borane-methyl sulfide in THF and the mixture was heated at reflux overnight. The reaction was then cooled to 0° C. and 10 mL of methanol was added. After the frothing ceased, 10 mL conc. HCl was added and the mixture was heated at reflux for 1 h. The reaction mixture was evaporated under reduced pressure and the residue was partitioned between 100 mL of ethyl acetate and 50 mL of 10% sodium hydroxide solution. The organic layer was washed with water, dried (MgSO$_4$), and evaporated. Chromatographic purification of the residue on chromatotron afforded 2.65 g (61%) of product as a pale yellow oil: $n_D^{25}=1.5829$.

PRE-EMERGENCE HERBICIDE EXAMPLES

As noted above, the compounds of this invention have been found to be surprisingly effective as herbicides, particularly pre-emergence herbicides.

The tests for pre-emergence herbicide activity are conducted as follows:

Topsoil is placed in an aluminum pan and compacted to a depth of 0.95 to 1.27 cm. from the top of the pan. On the top of the soil is placed a predetermined number of seeds of each of several monocotyledonous and dicotyledonous annual plant species and/or vegetative propagules of various perennial plant species. The soil required to level fill a pan after seeding or adding vegetative propagules is weighed into another pan. A known amount of the active ingredient dissolved or suspended in an organic solvent or water and applied in acetone or water as a carrier is thoroughly mixed with this cover soil, and the herbicide/soil mixture is used as a cover layer for the previously prepared pan. In Table 1 below for example, amount of active ingredient applied in the cover layer soil is equal to an application rate of 11.2 kg/ha. After treatment, the pans are moved to a greenhouse bench where they are watered from below as needed to give adequate moisture for germination and growth.

Approximately 10-14 days (usually 11 days) after seeding and treating, the pans are observed and the results (% inhibition) are recorded.

Table 1 below summarizes the results of the pre-emergence herbicidal activity tests of compounds of this invention in weeds. The herbicidal rating shown in Table 1 is the percent inhibition of each plant species according to the following rating system:

| Plant Response | Index |
| --- | --- |
| 0-24% inhibition | 0 |
| 25-49% inhibition | 1 |
| 50-74% inhibition | 2 |
| 75-100% inhibition | 3 |
| Species not planted | — |
| Species planted, no data | N |

The plant species usually regarded as weeds which are utilized in one set of tests, the data for which are shown in Table 1, are identified by letter headings above the columns in accordance with the following legend:

Yens—Yellow nutsedge
Anbg—Annual bluegrass
Sejg—Seedling johnsongrass
Dobr—Downy Brome
Bygr—Barnyardgrass
Mogl—Morningglory
Cobu—Cocklebur
Vele—Velvetleaf
Inmu—Indian mustard
Wibw—Wild buckwheat
Cath—Canada thistle
Colq—Common lambsquarters
Pesw—Pennsylvania smartweed
Rhqg—Rhizome quackgrass
Rhjg—Rhizome johnsongrass

TABLE 1

PRE-EMERGENCE HERBICIDE DATA

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
| --- | --- | --- | --- | --- | --- | --- | --- | --- | --- | --- | --- | --- | --- | --- | --- | --- |
| 1 | 11.21 | 1 | 3 | 3 | 3 | 3 | 3 | 3 | 3 | 3 | 3 | | | | | |
| 2 | 11.21 | 3 | | | 3 | 3 | 3 | 3 | 3 | | | 3 | 3 | 3 | 3 | 3 |
| 3 | 11.21 | 1 | 3 | 3 | 3 | 3 | 3 | 0 | 3 | 3 | 3 | | | | | |
| 4 | 11.21 | 2 | 3 | 3 | 3 | 3 | 2 | 0 | 3 | 3 | 3 | | | | | |
| 5 | 11.21 | 0 | | | 3 | 3 | 3 | 1 | 2 | | | 2 | 3 | 1 | 3 | — |
| 6 | 11.21 | 0 | | | 3 | 3 | 3 | 1 | 2 | | | 2 | 3 | 3 | 3 | — |
| 7 | 11.21 | 3 | | | 3 | 3 | 3 | 3 | 3 | | | 3 | 3 | 3 | 3 | 3 |
| 8 | 11.21 | 3 | | | 3 | 3 | 3 | 3 | 3 | | | 3 | 3 | 3 | 3 | 3 |
| 9 | 11.21 | 3 | | | 3 | 3 | 3 | 3 | 3 | | | 3 | 3 | 3 | 3 | — |
| 10 | 11.21 | 0 | | | 0 | 1 | 0 | 0 | 0 | | | 0 | 0 | N | 0 | 0 |
| 11 | 11.21 | 0 | 3 | 3 | 3 | 3 | 3 | 3 | 3 | 3 | 3 | | | | | |
| 12* | 11.21 | 2 | 3 | 3 | 3 | 3 | 3 | 3 | 3 | 3 | 3 | | | | | |

*DAMPING OFF-INMU AND WIBW; POOR GERMINATION-COBU

POST-EMERGENCE HERBICIDE EXAMPLES

The post-emergence herbicidal activity of some of the various compounds of this invention was demonstrated by greenhouse testing in the following manner. Topsoil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a bench in the greenhouse and watered from below as needed. After the plants reach the desired age (two to three weeks), each pan, is removed individually to a spraying chamber and sprayed by means of an atomizer, operating at a spray pressure of 170.3 kPa (10 psig) at the application rates noted. In the spray solution is an amount of an emulsifying agent mixture to give a spray solution or suspension which contains about 0.4% by volume of the emulsifier. The spray solution or suspension contains a sufficient amount of the active chemical in order to give application rates of the active ingredient corresponding to those shown in the Tables while applying a total amount of solution or suspension equivalent to 1870 L/Ha (200 gallons/acre). The pans were returned to the greenhouse and watered as before and the injury to the plants as compared to the control is observed at approximately 10-14 days (usually 11 days) and in some instances observed again at 24-28 days (usually 25 days) after spraying. The post-emergent herbicidal activity index used in Table 2 is as follows:

| Plant Response | Index |
| --- | --- |
| 0-24% inhibition | 0 |
| 25-49% inhibition | 1 |
| 50-74% inhibition | 2 |
| 75-99% inhibition | 3 |
| 100% inhibition | 4 |
| Species not planted | — |
| Species planted, no data | N |

TABLE 2

POST-EMERGENCE HERBICIDE DATA

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 1 | 11.21 | 0 | 0 | 1 | 0 | 0 | 1 | 0 | 1 | 2 | 2 | 0 | 0 | 0 | 0 | N |
| 2 | 11.21 | 0 |   |   | 0 | 0 | 0 | 0 | 0 |   |   |   |   |   |   |   |
| 3 | 11.21 | 0 | 2 | 2 | 0 | 2 | 0 | 0 | 2 | 0 | 0 |   |   |   |   |   |
| 4 | 11.21 | 0 | 0 | 2 | 0 | 0 | 1 | 2 | 2 | 0 | 2 |   |   |   |   |   |
| 5 | 11.21 | 0 |   |   | 0 | 0 | 0 | 0 | 0 |   |   | 0 | 0 | 0 | 0 | 0 |
| 6 | 11.21 | 0 |   |   | 0 | 0 | 1 | 0 | 0 |   |   | 0 | 0 | 0 | 0 | 0 |
| 7 | 11.21 | 0 |   |   | 0 | 2 | 1 | 0 | 1 |   |   | — | 1 | 0 | 0 | N |
| 8 | 11.21 | 0 |   |   | 0 | 1 | 1 | 0 | 0 |   |   | 0 | 2 | 0 | 0 | 0 |
| 9 | 11.21 | 0 |   |   | 0 | 2 | 1 | 1 | 1 |   |   | 1 | N | 0 | 0 | 0 |
| 10 | 11.21 | 0 |   |   | 0 | 0 | 0 | 0 | 0 |   |   | 0 | 0 | N | 0 | 0 |
| 11 | 11.21 | 0 | 0 | 0 | 0 | 1 | 0 | 0 | 2 | 1 | 2 |   |   |   |   |   |
| 12* | 11.21 | 0 | 2 | 2 | 0 | 2 | 2 | 1 | 2 | 2 | 2 |   |   |   |   |   |

*DAMPING OFF-INMU AND WIBW; POOR GERMINATION-COBU

PRE-EMERGENCE CROP AND WEED PLANT HERBICIDE ACTIVITY

The compounds of this invention were further tested by utilizing the above procedure for pre-emergence testing on the following plant species, i.e., on weeds in the presence of crop plants. The following plant species were used in these tests.

| | |
|---|---|
| Sobe - Soybean | Colq - Common lambsquarters |
| Sube - Sugarbeet | Pesw - Pennsylvania smartweed |
| Whez - Wheat | Vele - Velvetleaf |
| Rice - Rice | Dobr - Downy brome |
| Grso - Grain sorghum | Rape - Oilseed rape |
| Cobu - Cocklebur | Bygr - Barnyardgrass |
| Wibw - Wild buckwheat | Lacg - Large crabgrass |
| Mogl - Morningglory | Grft - Green foxtail |
| Hese - Hemp sesbania | Corn - Corn |
| Cotz - Cotton | Prmi - Proso millet |
| Jiwe - Jimsonweed | |

The results of these tests are summarized in Table 3 below, in which the rating codes are the same as those used in Table 1.

TABLE 3

| Ex. No. | Rate kg/ha | Sobe | Cotz | Rape | Cobu | Wibw | Mogl | Hesc | Jiwe | Vele | Whez | Rice | Grso | Corn | Dobr | Prmi | Bygr | Lacg | Grft | Sube | Colq | Pesw |
|---|---|---|---|---|---|---|---|---|---|---|---|---|---|---|---|---|---|---|---|---|---|---|
| 1 | 5.6050 | 3 | 2 | 3 | 1 | 3 | 3 | 3 | 3 | 2 | 3 | 3 | 3 | 3 | 3 | 3 | 3 | 3 | 3 | 3 | 3 | 3 |
|   | 1.1210 | 2 | 0 | 2 | 1 | 3 | 3 | 3 | 2 | 2 | 3 | 3 | 3 | 1 | 3 | 3 | 3 | 3 | 3 | 3 | 3 | 3 |
|   | 0.2803 | 1 | 0 | 0 | 0 | 0 | 2 | 0 | 0 | 0 | 1 | 0 | 3 | 0 | 0 | 0 | 1 | 0 | 2 | 3 | 3 | 3 |
|   | 0.0701 | 0 | 0 | 0 | 1 | 3 | 0 | 0 | 0 | 0 | 0 | 3 | 0 | 1 | 3 | 0 | 0 | 0 | 0 | 0 | 1 | 2 |
|   | 0.0175 | 0 |   |   | 0 | 3 | 3 | 3 | 0 | 3 | 3 | 3 | 3 | 3 | 3 | 3 | 3 | 3 | 3 | 1 | N | 1 |
| 2 | 5.6050 | 3 |   |   | 0 | 2 | 3 | 3 |   | 1 | 3 | 3 | 3 | 1 | 3 | 3 | 3 | 3 | 3 | 0 | 2 | 0 |
|   | 1.1210 | 3 |   |   | 3 | 0 | 3 | 2 |   | 0 | 3 | 3 | 3 | 0 | 3 | 3 | 3 | 3 | 3 | 0 | 1 | 0 |
|   | 0.5605 | 3 |   |   | 0 | 0 | 3 | 1 |   | 0 | 3 | 0 | 2 | 1 | 1 | N | 2 | 3 | 3 | 0 | 1 | 1 |
|   | 0.2803 | 3 |   |   | 0 | 0 | 3 | 0 |   | 0 | 3 | 0 | 1 | 0 | 3 | 1 | 2 | 3 | 3 | 0 | 0 | 0 |
|   | 0.1401 | 1 |   |   | Z | Z | 0 | 0 |   | 0 | 1 | 0 | 0 | 0 | 2 | 0 | 2 | 0 | 0 | 0 | 0 | 0 |
|   | 0.0701 | 0 |   |   | 0 | 0 | 0 | 0 |   | 0 | 3 | 0 | 0 | 0 | 0 | 0 | 0 | 0 | 0 | 0 | 0 | 1 |
|   | 0.0350 | Z |   |   | 0 | 0 | 0 | 0 |   | 0 | 0 | 0 | 0 | 0 | 0 | 0 | 0 | 0 | 0 | 0 | 0 | 0 |
|   | 0.0175 | 0 |   |   | 0 | 0 | 0 | 0 |   | 0 | 0 | 0 | 0 | 0 | 0 | 0 | 0 | 0 | 0 | 0 | 0 | 0 |
|   | 0.0087 | 0 |   |   | 0 | 0 | 0 | 0 |   | 0 | 0 | 0 | 0 | 0 | 0 | 0 | 0 | 0 | 0 |   |   |   |
|   | 0.0044 | 0 |   |   | 0 | 0 | 0 | 0 |   | 0 | 0 | 0 | 0 | 0 | 0 | 0 | 0 | 0 | 0 |   |   |   |
| 3 | 5.6050 | 3 | 1 | 3 | 2 | 3 | 3 | 3 | 3 | 3 | 3 | 3 | 3 | 3 | 3 | 3 | 3 | 3 | 3 | 3 | 3 | 3 |
|   | 1.1210 | 0 | 1 | 0 | 0 | 0 | 2 | 0 | 2 | 0 | 0 | 0 | 0 | 0 | 0 | 0 | 3 | 0 | 0 | 0 | 0 | 0 |
|   | 0.2803 | 1 | 1 | 0 | 0 | 0 | 1 | 1 | 0 | 1 | 0 | 0 | 0 | 0 | 0 | 1 | 3 | 1 | 1 | 0 | 0 | 1 |
|   | 0.0701 | 0 | 0 | 0 | 0 | 0 | 0 | 0 | 1 | 0 | 3 | 3 | 3 | 0 | 3 | 3 | 3 | 3 | 0 | 0 | 0 | 0 |
|   | 0.0175 | 0 |   |   | 0 | 3 | 0 | 0 | 0 | 0 | 3 | 0 | 0 | 0 | 0 | 2 | 3 | 2 | 3 | 0 | 0 | 1 |
| 4 | 5.6050 | 2 | 1 |   | 0 | 0 | 0 | 0 | 0 | 0 | 0 | 0 | 0 | 0 | 0 | 0 | 0 | 0 | 0 | 0 | 0 | 1 |
|   | 1.1210 | 0 | 1 |   | 0 | 0 | 0 | 0 | 1 | 0 | 0 | 0 | 0 | 0 | 0 | 0 | 0 | 0 | 0 | 0 | 0 | 1 |
|   | 0.2803 | 0 | 0 |   | 0 | 0 | 0 | 0 | 0 | 0 | 0 | 0 | 0 | 0 | 0 | 0 | 0 | 0 | 0 | 0 | 0 | N |
|   | 0.0701 | 0 | 1 |   | 0 | 3 | 3 | 0 | 3 | 3 | 3 | 3 | 3 | 0 | 3 | 3 | 3 | 3 | 3 | 3 | 1 | 2 |
|   | 0.0175 | 0 | 1 |   | 0 | 0 | 0 | 1 | 1 | 0 | 0 | 0 | 0 | 1 | 0 | 0 | 0 | 0 | 0 | 0 | 0 | N |
| 5 | 5.6050 | 3 | 0 |   | 0 | 0 | 3 | 0 |   | 0 | 0 | 0 | 0 | 0 | 1 | 0 | 0 | 2 | 0 | 0 | 1 | 0 |
|   | 1.1210 | 0 | Z |   | 1 | 0 | 0 | 0 |   | 0 | 0 | 0 | 0 | 0 | 0 | 0 | 0 | 0 | 0 | 0 | 0 | 0 |
|   | 0.5605 | 0 | 0 |   | 0 | 0 | 0 | 0 |   | 0 | 0 | 0 | 0 | 0 | 0 | 0 | 0 | 0 | 0 | 0 | 0 | 0 |
|   | 0.2803 | 0 |   |   | 0 | 0 | 0 | 0 |   | 0 | 0 | 0 | 0 | 0 | 0 | 0 | 0 | 0 | 0 | 0 | Z | 0 |
|   | 0.1401 | 0 |   |   | 0 | 0 | 0 | 0 |   | 0 | 0 | 0 | 0 | 0 | 0 | 0 | 0 | 0 | 0 | Z | 0 | 0 |
|   | 0.0701 | 0 |   |   | 0 | 0 | 0 | 0 |   | 0 | 0 | 0 | 0 | 0 | 0 | 0 | 0 | 0 | 0 | 0 | 0 | 0 |
|   | 0.0350 | 0 |   |   | 0 | 3 | 3 | 2 |   | 2 | 3 | 3 | 1 | 1 | 0 | 0 | 3 | 3 | 3 | 3 | 3 | 3 |
|   | 0.0175 | 3 |   |   | 0 | 0 | 3 | 0 |   | 1 | 3 | 3 | 0 | 0 | 3 | 0 | 3 | 0 | 0 | 0 | 0 | 0 |
| 6 | 5.6050 | 0 | 0 |   | 1 | 1 | 3 | 0 |   | 0 | 3 | 3 | 0 | 0 | 1 | 0 | 3 | 0 | 0 | 0 | 0 | 0 |
|   | 1.1210 | 0 | 0 |   | 0 | 0 | 0 | 0 |   | 0 | 0 | 0 | 0 | 0 | 0 | 0 | 0 | 0 | 0 | 0 | 0 | 0 |
|   | 0.5605 | 0 | 0 |   | 0 | 0 | 0 | 0 |   | 0 | 0 | 0 | 0 | 0 | 0 | 0 | 0 | 0 | 0 | 0 | 0 | 0 |
|   | 0.2803 | 0 |   |   | 0 | 0 | 0 | 0 |   | 0 | 0 | 0 | 0 | 0 | 0 | 0 | 0 | 0 | 0 | 0 | 0 | 0 |
|   | 0.1401 | 0 |   |   | 0 | 0 | 0 | 0 |   | 0 | 0 | 0 | 0 | 0 | 0 | 0 | 0 | 0 | 0 | 0 | Z | 0 |
|   | 0.0701 | 0 |   |   | 0 | Z | 0 | 0 |   | 0 | Z | 0 | Z | 0 | 0 | Z | 0 | Z | 0 | 0 | Z | 0 |
|   | 0.0350 | Z |   |   | 2 | 0 | 2 | 0 |   | 0 | 0 | 0 | 0 | 0 | 0 | 0 | 0 | 0 | 0 | 3 | 3 | 3 |
|   | 0.0175 | 0 |   |   | 0 | 0 | 3 | 0 |   | 0 | 0 | 3 | 0 | 0 | 0 | 0 | 0 | 0 | 0 | 3 | 3 | 3 |
| 7 | 5.6050 | 3 | 0 |   | 1 | 3 | 3 | 0 |   | 3 | 3 | 3 | 3 | 3 | 3 | 3 | 3 | 3 | 3 | 3 | 3 | 1 |
|   | 1.1210 | 2 | 0 |   | 0 | 1 | 0 | 0 |   | 0 | 1 | 3 | 3 | 0 | 3 | 3 | 3 | 2 | 3 | 0 | 0 | 1 |
|   | 0.5605 | 2 | 0 |   | 0 | 0 | 0 | 0 |   | 0 | 0 | 0 | 0 | 0 | 0 | 0 | 0 | 0 | 0 | 0 | 0 | 0 |
|   | 0.2803 | 0 |   |   | 0 | 0 | 0 | 0 |   | 0 | 0 | 0 | 0 | 0 | 0 | 0 | 0 | 0 | 0 | 0 | 0 | 0 |
|   | 0.1401 | 0 |   |   | 0 | 0 | 0 | 0 |   | 0 | 0 | 0 | 0 | 0 | 0 | 0 | 0 | 0 | 0 | 0 | 0 | 0 |
|   | 0.0701 | 0 |   |   | 0 | 0 | 0 | 0 |   | 0 | 0 | 0 | 0 | 0 | 0 | 0 | 0 | 0 | 0 | 0 | 0 | 0 |
|   | 0.0350 | 0 |   |   | 0 | 0 | 0 | 0 |   | 0 | 0 | 0 | 0 | 0 | 0 | 0 | 0 | 0 | 1 | 0 | 0 | 0 |
|   | 0.0175 | 0 |   |   | 0 | 1 | 0 | 0 |   | 0 | 0 | 0 | 0 | 0 | 0 | 0 | 0 | 0 | 0 | 0 | 0 | 0 |

TABLE 3-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw |
|---|---|---|---|---|---|---|---|---|---|---|---|---|---|---|---|---|---|---|---|---|---|---|
| | 0.0087 | 0 | | | 0 | 0 | 0 | 0 | | 0 | 0 | 0 | 0 | 0 | 0 | 0 | 0 | 0 | 0 | N | N | N |
| | 0.0044 | 0 | | | 0 | 0 | 0 | 0 | | 0 | 0 | 0 | 0 | 0 | 0 | 0 | 0 | 0 | 0 | 0 | 0 | 0 |
| 8 | 5.6050 | 3 | | | 3 | 3 | 3 | 3 | | 3 | 3 | 3 | 3 | 3 | 3 | 3 | 3 | 3 | 3 | 3 | 3 | 3 |
| | 1.1210 | 3 | | | 1 | 0 | 3 | 3 | | 0 | 3 | 3 | 3 | 3 | 3 | 3 | 3 | 3 | 3 | 3 | 3 | 3 |
| | 0.5605 | 2 | | | 1 | 0 | 3 | 0 | | 3 | 3 | 3 | 3 | 3 | 3 | 3 | 3 | 3 | 3 | 3 | 3 | 3 |
| | 0.2803 | 2 | | | 1 | 0 | 1 | 0 | | 0 | 2 | 3 | 3 | 0 | 3 | 3 | 3 | 3 | 3 | 2 | 2 | 1 |
| | 0.1401 | 0 | | | 2 | 0 | 0 | 0 | | 0 | 3 | 3 | 0 | 0 | 2 | 2 | 3 | 3 | 3 | 1 | 0 | 2 |
| | 0.0701 | 1 | | | 0 | 0 | 1 | 0 | | 0 | 0 | 0 | 0 | 0 | 0 | N | 3 | 1 | 3 | 1 | 0 | 1 |
| | 0.0350 | 0 | | | 0 | 0 | 0 | 0 | | 0 | 0 | 0 | 0 | 0 | 0 | 0 | 0 | 0 | 0 | 0 | 0 | 2 |
| | 0.0175 | 0 | | | 0 | 0 | 0 | 0 | | 0 | 0 | 0 | 0 | 0 | 0 | 0 | 0 | 0 | 0 | 0 | 0 | 0 |
| | 0.0087 | N | | | 0 | 0 | 0 | 0 | | 0 | 0 | 0 | 0 | 0 | 0 | 0 | 0 | 0 | 0 | 0 | 0 | 0 |
| | 0.0044 | 0 | | | 0 | 0 | 0 | 0 | | 0 | 0 | 0 | 0 | 0 | 0 | 0 | 0 | 0 | 0 | 0 | 0 | 0 |
| 9 | 5.6050 | 3 | | | 2 | 3 | 3 | 3 | | 3 | 3 | 3 | 3 | 3 | 3 | 3 | 3 | 3 | 3 | 3 | 3 | 3 |
| | 1.1210 | 2 | | | 3 | 3 | 3 | 3 | | 0 | 3 | 3 | 3 | 3 | 3 | 3 | 3 | 3 | 3 | 3 | 3 | 3 |
| | 0.5605 | 1 | | | 1 | 2 | 2 | 2 | | 3 | 3 | 3 | 3 | 3 | 3 | 3 | 3 | 3 | 3 | 3 | 3 | 3 |
| | 0.2803 | 1 | | | 0 | 0 | 1 | 1 | | 0 | 3 | 3 | 2 | 0 | 2 | 2 | 2 | 2 | 3 | 2 | 2 | 2 |
| | 0.1401 | 1 | | | 0 | 0 | 0 | 0 | | 0 | 0 | 0 | 0 | 0 | 0 | 1 | 0 | 1 | 0 | 1 | 1 | 1 |
| | 0.0701 | 0 | | | 0 | 0 | 0 | 0 | | 0 | 0 | 0 | 0 | 0 | 0 | 0 | 0 | 0 | 3 | 0 | 0 | 2 |
| | 0.0350 | 1 | | | 0 | 1 | 0 | 0 | | 3 | 3 | 3 | 3 | 3 | 3 | 3 | 3 | 3 | 3 | 3 | 3 | 3 |
| | 0.0175 | 0 | | | 0 | N | 0 | 0 | | 0 | 0 | 0 | 0 | 0 | 0 | 0 | 0 | 0 | 2 | 0 | 0 | 0 |
| | 0.0087 | 0 | | | 0 | N | 0 | 0 | | 0 | 0 | 0 | 0 | 0 | 0 | 0 | 0 | 0 | 0 | 0 | 0 | 0 |
| | 0.0044 | 0 | | | 0 | 1 | 0 | 0 | | 1 | 0 | 0 | 0 | 0 | 0 | 0 | 0 | 0 | 0 | 0 | 0 | 0 |
| 11 | 5.6050 | 3 | 1 | 2 | 2 | 3 | 3 | 0 | 3 | 3 | 3 | 3 | 3 | 2 | 3 | 3 | 3 | 3 | 3 | 3 | 3 | 3 |
| | 1.1210 | 0 | 0 | 1 | 2 | 2 | 0 | 1 | 1 | 0 | 3 | 1 | 2 | 1 | 1 | 2 | 0 | 0 | 2 | 1 | 1 | 2 |
| | 0.2803 | 1 | 0 | 0 | 0 | 0 | 0 | 2 | 0 | 3 | 3 | 3 | 3 | 3 | 3 | 3 | 3 | 3 | 3 | 3 | 3 | 3 |
| | 0.0701 | 0 | 0 | 0 | 0 | 0 | 0 | 0 | 0 | 0 | 0 | 0 | 0 | 0 | 0 | 0 | 0 | 0 | 0 | 0 | 0 | 0 |
| | 0.0175 | 0 | Z | 0 | 0 | 0 | 0 | 0 | 0 | 1 | 0 | 0 | 0 | 0 | N | 0 | 0 | 0 | 0 | 0 | 0 | 0 |
| 12 | 5.6050 | 3 | 3 | 3 | 1 | 3 | 3 | 3 | 3 | 3 | 3 | 3 | 3 | 3 | 3 | 3 | 3 | 3 | 3 | 3 | 3 | 3 |
| | 1.1210 | 3 | 1 | 3 | 2 | 1 | 2 | 2 | 1 | 1 | 3 | 3 | 3 | 3 | 1 | 3 | 3 | 3 | 3 | 3 | 3 | 3 |
| | 0.2803 | 1 | 0 | 0 | 0 | 0 | 0 | 0 | 0 | 3 | 3 | 3 | 3 | 3 | 0 | 3 | 3 | 3 | 3 | 0 | 0 | 0 |
| | 0.0701 | 0 | 0 | 0 | 0 | 0 | 0 | 0 | 0 | 0 | 0 | 0 | 0 | 0 | 0 | 0 | 0 | 0 | 3 | 0 | 0 | 1 |
| | 0.0175 | 0 | 0 | 0 | 0 | 0 | 0 | 0 | 0 | 0 | 0 | 0 | 0 | 0 | 0 | 0 | 0 | 0 | 3 | 0 | Z | 1 |
| | 0.0087 | 0 | 0 | 0 | 0 | 0 | 0 | 0 | 0 | 0 | 0 | 0 | 0 | 0 | 0 | 0 | 0 | 0 | 0 | 0 | N | 1 |

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, and polymethylene bisnaphthalene sulfonate. Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably from 5-20 parts) of active ingredient, from about 0.25 to 25 parts (preferably 1-15 parts) of wetting agent, from about 0.25 to 25 parts (preferably 1.0-15 parts) of dispersant and from 5 to about 95 parts (preferably 5-50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1-10% by weight.

Aqueous suspensions or emulsions may be prepared by stirring a nonaqueous solution of a water-insoluble active ingredient and an emulsification agent with water until uniform and then homogenizing to give stable emulsion of very finely divided particles. The resulting concentrated aqueous suspension is characterized by its extremely small particle size, so that when diluted and sprayed, coverage is very uniform. Suitable concentrations of these formulations contain from about 0.1-60% preferably 5-50% by weight of active ingredient, the upper limit being determined by the solubility limit of active ingredient in the solvent.

Concentrates are usually solutions of active ingredient in water-immiscible or partially water-immiscible solvents together with a surface active agent. Suitable solvents for the active ingredient of this invention include dimethylformamide, dimethylsulfoxide, N-methylpyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5-60 parts) active ingredient, about 0.25 to 50 parts (preferably 1-25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate extender, a surface active agent such as those listed hereinbefore can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, carbamates, acetamides, acetanilides, uracils, acetic acid or phenol derivatives, thiolcarbamates, triazoles, benzoic acids, nitriles, biphenyl ethers and the like such as:

Hetetocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2-dioxide
3-Amino-1,2,4-triazole
6,7-Dihydrodipyrido(1,2-:2′,1′-c)-pyrazidiinium salt
5-Bromo-3-isopropyl-6-methyluracil
1,1′-Dimethyl-4,4′-bipyridinium
2-(4-isopropyl-4-methyl-5-oxo-2-imidazolin-2-yl)-3-quinolinecarboxylic acid
Isopropylamine salt of 2-(4-isopropyl-4-methyl-5-oxo-2-imidazolin-2-yl)nicotinic acid
Methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate Ureas N-(4-chlorophenoxy) phenyl-N,N-dimethylurea
N,N-dimethyl-N′-(3-chloro-4-methylphenyl) urea
3-(3,4-dichlorophenyl)-1,1-dimethylurea
1,3-Dimethyl-3-(2-benzothiazolyl) urea
3-(p-Chlorophenyl)-1,1-dimethylurea
1-Butyl-3-(3,4-dichlorophenyl)-1-methylurea 2-Chloro-N[(4-methoxy-6-methyl-1,3,5-triazin-2-yl)aminocarbonyl]-benzenesulfonamide
Methyl 2-(((((4,6-dimethyl-2-pyrimidinyl)amino)carbonyl)amino)sulfonyl) benzoate
Ethyl 2-[methyl 2-(((((4,6-dimethyl-2-pyrimidinyl)amino)carbonyl)amino)sulfonyl)] benzoate
Methyl-2((4,6-dimethoxy pyrimidin-2-yl)aminocarbonyl)amino sulfonyl methyl) benzoate
Methyl 2-(((((4-methoxy-6-methyl-1,3,5-triazin-2-yl)amino)carbonyl)amino)sulfonyl) benzoate

Carbamates/Thiolcarbamates

2-Chloroallyl diethyldithiocarbamate
S-(4-chlorobenzyl)N,N-diethylthiolcarbamate
Isopropyl N-(3-chlorophenyl)carbamate
S-2,3-dichloroallyl N,N-diisopropylthiolcarbamate
S-N,N-dipropylthiolcarbamate
S-propyl N,N-dipropylthiolcarbamate
S-2,3,3-trichloroallyl-N,N-diisopropylthiolcarbamate

Acetamides/Acetanilides/Anilines/Amides

2-Chloro-N,N-diallylacetamide
N,N-dimethyl-2,2-diphenylacetamide
N-(2,4-dimethyl-5-[[[(trifluoromethyl)sulfonyl]amino]-phenyl]acetamide
N-Isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide
α,α,α-Trifluoro-2,6-dinitro-N,N-dipropyl-p-toluidine
N-(1,1-dimethylpropynyl)-3,5-dichlorobenzamide

Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol
N-(phosphonomethyl)glycine and its salts.
Butyl (R)-2-[4-[(5-(trifluoromethyl)-2-pyridinyl)oxy]-phenoxy]-propanoate

Ethers 2,4-Dichlorophenyl-4-nitrophenyl ether
2-Chloro-δ,δ,δ-trifluoro-p-tolyl-3-ethoxy-4-nitrodiphenyl ether
5-(2-chloro-4-trifluoromethylphenoxy)-N-methylsulfonyl 2-nitrobenzamide
1'-(Carboethoxy) ethyl 5-[2-chloro-4-(trifluoromethyl)-phenoxy]-2-nitrobenzoate

Miscellaneous 2,6-Dichlorobenzonitrile
Monosodium acid methanearsonate
Disodium methanearsonate
2-(2-chlorophenyl)methyl-4,4-dimethyl-3-isoxazolidinone
7-oxabicyclo(2.2.1)heptane, 1-methyl-4-(1-methylethyl)-2-(2-methylphenylmethoxy)-,exo- Fertilizers useful in combination with the active ingredients include, for example ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

| I. Emulsifiable Concentrates | | |
|---|---|---|
| | | Weight Percent |
| A. | Compound of Example No. 3 | 11.0 |
| | Free acid of complex organic phosphate or aromatic or aliphatic hydrophobe base (e.g., GAFAC RE-610, registered trademark of GAF Corp.) | 5.59 |
| | Polyoxyethylene/polyoxypropylene block copolymer with butanol (e.g., Tergitol XH, registered trademark of Union Carbide Corp.) | 1.11 |
| | Phenol | 5.34 |
| | Monochlorobenzene | 76.96 |
| | | 100.00 |
| B. | Compound of Example No. 11 | 25.00 |
| | Free acid of complex organic phosphate of aromatic or aliphatic hydrophobe base (e.g., GAFAC RE-610) | 5.00 |
| | Polyoxyethylene/polyoxypropylene block copolymer with butanol (e.g., Tergitol XH) | 1.60 |
| | Phenol | 4.75 |
| | Monochlorobenzene | 63.65 |
| | | 100.00 |

| II. Flowables | | |
|---|---|---|
| | | Weight Percent |
| A. | Compound of Example No. 12 | 25.0 |
| | Methyl cellulose | 0.3 |
| | Silica aerogel | 1.5 |
| | Sodium lignosulfonate | 3.5 |
| | Sodium N-methyl-N-oleyl taurate | 2.0 |
| | Water | 67.7 |
| | | 100.0 |
| B. | Compound of Example No. 9 | 45.0 |
| | Methyl cellulose | .3 |
| | Silica aerogel | 1.5 |
| | Sodium lignosulfonate | 3.5 |
| | Sodium N-methyl-N-oleyl taurate | 2.0 |
| | Water | 47.7 |
| | | 100.0 |

| III. Wettable Powders | | |
|---|---|---|
| | | Weight Percent |
| A. | Compound of Example No. 5 | 25.0 |
| | Sodium lignosulfonate | 3.0 |
| | Sodium N-methyl-N-oleyl-taurate | 1.0 |
| | Amorphous silica (synthetic) | 71.0 |
| | | 100.0 |
| B. | Compound of Example 10 | 80.00 |
| | Sodium dioctyl sulfosuccinate | 1.25 |
| | Calcium lignosulfonate | 2.75 |
| | Amorphous silica (synthetic) | 16.00 |
| | | 100.00 |
| C. | Compound of Example No. 6 | 10.0 |
| | Sodium lignosulfonate | 3.0 |
| | Sodium N-methyl-N-oleyl-taurate | 1.0 |
| | Kaolinite clay | 86.0 |
| | | 100.00 |

| IV. Dusts | | |
|---|---|---|
| | | Weight Percent |
| A. | Compound of Example No. 7 | 2.0 |
| | Attapulgite | 98.0 |
| | | 100.0 |
| B. | Compound of Example No. 4 | 60.0 |
| | Montmorillonite | 40.0 |
| | | 100.0 |
| C. | Compound of Example No. 2 | 30.0 |
| | Ethylene glycol | 1.0 |
| | Bentonite | 69.0 |
| | | 100.0 |
| D. | Compound of Example No. 1 | 1.0 |
| | Diatomaceous earth | 99.0 |
| | | 100.0 |

| V. Granules | | |
|---|---|---|
| | | Weight Percent |
| A. | Compound of Example No. 8 | 15.0 |
| | Granular attapulgite (20/40 mesh) | 85.0 |
| | | 100.0 |
| B. | Compound of Example No. 5 | 30.0 |
| | Diatomaceous earth (20/40) | 70.0 |
| | | 100.0 |
| C. | Compound of Example No. 12 | 1.0 |
| | Ethylene glycol | 5.0 |
| | Methylene blue | 0.1 |
| | Pyrophyllite | 93.9 |
| | | 100.0 |
| D. | Compound of Example No. 7 | 5.0 |
| | Pyrophyllite (20/40) | 95.0 |
| | | 100.0 |

When operating in accordance with the present invention, effective amounts of the compounds of this invention are applied to the soil containing the seeds, or vegetative propagules or may be incorporated into the soil media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages. The exact amount of active ingredient to be employed is dependent upon various factors, including the plant species and stage of development thereof, the type and condition of soil, the amount of rainfall and the specific compounds employed. In selective preemergence application or to the soil, a dosage of from about 0.02 to about 11.2 kg/ha, preferably from about 0.1 to about 5.60 kg/ha, is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in *Webster's New International Dictionary*, Second Edition, Unabridged (1961). Thus, the term refers to any substance or medium in which vegetation may take root and grow, and includes not only earth but also compost, manure, muck, humus, loam, silt, mire, clay, sand, and the like, adapted to support plant growth.

Although the invention is described with respect to specific modifications, the details thereof are not to be construed as limitations.

We claim:

1. A compound represented by the formula

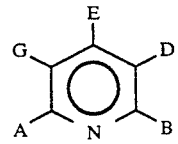

wherein:
one of A and B is selected from the group consisting of fluorinated methyl and chlorofluorinated methyl radicals, and the other is selected from the group consisting of fluorinated methyl, chlorofluorinated methyl and lower alkyl radicals;
E is selected from the group consisting of $C_1$–$C_7$ alkyl, $C_2$–$C_7$ alkenyl, $C_3$–$C_7$ cycloalkyl, $C_3$–$C_7$ cycloalkyl $C_1$–$C_7$ alkyl, $C_1$–$C_7$ haloalkyl, and $C_1$–$C_7$ alkylthio $C_1$–$C_7$ alkyl radicals;
G is selected from the group consisting of hydroxycarbonyl, $C_1$–$C_7$ alkoxycarbonyl and $C_1$–$C_7$ alkylthio carbonyl; and
D is —NRR' in which R and R' are the same or different lower alkyl groups, each optionally substituted with one or more groups selected from halo, amino, hydroxy, $C_1$–$C_7$ alkylthio, $C_1$–$C_7$ alkylsulfonyl, cyclopropylmethyl, and $C_1$–$C_7$ alkoxy radicals.

2. A compound according to claim 1 wherein one of A and B is trifluoromethyl and the other is difluoromethyl.

3. A compound according to claim 2 wherein E is selected from the group consisting of 2-methylpropyl, cyclobutyl, and cyclopropylmethyl.

4. A compound according to claim 3 wherein G is methoxycarbonyl.

5. A compound according to claim 4 wherein R is methyl and R' is selected from methyl, ethyl, and cyclopropylmethyl.

6. A preemergent herbicidal composition containing a diluent and an effective herbicidal amount of a compound represented by the formula

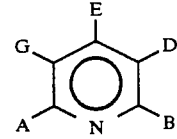

wherein:
one of A and B is selected from the group consisting of fluorinated methyl and chlorofluorinated methyl radicals, and the other is selected from the group consisting of fluorinated methyl, chlorofluorinated methyl and lower alkyl radicals;
E is selected from the group consisting of $C_1$–$C_7$ alkyl, $C_2$–$C_7$ alkenyl, $C_3$–$C_7$ cycloalkyl, $C_3$–$C_7$ cycloalkyl $C_1$–$C_7$ alkyl, $C_1$–$C_7$ haloalkyl, and $C_1$–$C_7$ alkylthio $C_1$–$C_7$ alkyl radicals;
G is selected from the group consisting of hydroxycarbonyl, $C_1$–$C_7$ alkoxycarbonyl and $C_1$–$C_7$ alkylthio carbonyl; and
D is —NRR' in which R and R' are the same or different lower alkyl groups, each optionally substituted with one or more groups selected from halo, amino, hydroxy, $C_1$–$C_7$ alkylthio, $C_1$–$C_7$ alkylsulfonyl, cyclopropylmethyl, and $C_1$–$C_7$ alkoxy radicals.

7. A composition according to claim 6 wherein one of A and B is trifluoromethyl and the other is difluoromethyl.

8. A composition according to claim 7 wherein E is selected from the group consisting of 2-methylpropyl, cyclobutyl, and cyclopropylmethyl.

9. A composition according to claim 8 wherein G is methoxycarbonyl.

10. A composition according to claim 9 wherein R is methyl and R' is selected from methyl, ethyl, and cyclopropylmethyl.

11. A method of controlling undesired vegetation which comprises applying to the plant locus prior to plant emergence an effective amount of a compound represented by the formula

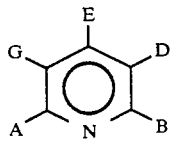

wherein:
one of A and B is selected from the group consisting of fluorinated methyl and chlorofluorinated methyl radicals, and the other is selected from the group consisting of fluorinated methyl, chlorofluorinated methyl and lower alkyl radicals;
E is selected from the group consisting of $C_1$–$C_7$ alkyl, $C_2$–$C_7$ alkenyl, $C_3$–$C_7$ cycloalkyl, $C_3$–$C_7$ cycloalkyl $C_1$–$C_7$ alkyl, $C_1$–$C_7$ haloalkyl, and $C_1$–$C_7$ alkylthio $C_1$–$C_7$ alkyl radicals;
G is selected from the group consisting of hydroxycarbonyl, $C_1$–$C_7$ alkoxycarbonyl and $C_1$–$C_7$ alkylthio carbonyl; and
D is —NRR' in which R and R' are the same or different lower alkyl groups, each optionally substituted with one or more groups selected from halo, amino, hydroxy, $C_1$–$C_7$ alkylthio, $C_1$–$C_7$ alkylsulfonyl, cyclopropylmethyl, and $C_1$–$C_7$ alkoxy radicals.

12. A method according to claim 11 wherein one of A and B is trifluoromethyl and the other is difluoromethyl.

13. A method according to claim 12 wherein E is selected from the group consisting of 2-methylpropyl, cyclobutyl, and cyclopropylmethyl.

14. A method according to claim 13 wherein G is methoxycarbonyl.

15. A method according to claim 14 wherein R is methyl and R' is selected from methyl, ethyl, and cyclopropylmethyl.

16. The methyl ester of 4-(cyclopropylmethyl)-2-difluoromethyl)-5-(dimethylamino)-6-(trifluoromethyl)-3-pyridinecarboxylic acid.

17. A preemergent herbicidal composition containing a diluent and an effective amount of the methyl ester of 4-(cyclopropylmethyl)-2-difluoromethyl)-5-(dimethylamino)-6-(trifluoromethyl)-3-pyridinecarboxylic acid.

18. A method of controlling undesired vegetation which comprise applying to the plant locus prior to plant emergence an effective amount of the methyl ester of 4-(cyclopropylmethyl)-2-difluoromethyl)-5-(dimethylamino)-6-(trifluoromethyl)-3-pyridinecarboxylic acid.

19. The methyl ester of 4-(cyclopropylmethyl)-2-(difluoromethyl-5-(ethylmethylamino)-6-(trifluoromethyl)-3-pyridinecarboxylic acid.

20. A preemergent herbicidal composition containing a diluent and an effective amount of the methyl ester of 4-(cyclopropylmethyl)-2-(difluoromethyl-5-(ethylmethylamino)-6-(trifluoromethyl)-3-pyridinecarboxylic acid.

21. A method of controlling undesired vegetation which comprises applying to the plant locus prior to plant emergence an effective amount of the methyl ester of 4-(cyclopropylmethyl)-2-(difluoromethyl-5-(ethylmethylamino)-6-trifluoromethyl)-3-pyridinecarboxylic acid.

* * * * *